United States Patent [19]

Childers et al.

[11] Patent Number: 5,032,186
[45] Date of Patent: Jul. 16, 1991

[54] WASHER-STERILIZER

[75] Inventors: Robert W. Childers; Conrad Geibel, both of Erie, Pa.

[73] Assignee: American Sterilizer Company, Erie, Pa.

[21] Appl. No.: 290,408

[22] Filed: Dec. 27, 1988

[51] Int. Cl.$^5$ .................................................. B08B 3/00
[52] U.S. Cl. ..................................... 134/25.2; 134/10; 134/18; 134/30; 134/36; 134/37; 134/56 R; 134/25.1; 134/95; 134/102; 422/26; 422/33; 422/295
[58] Field of Search ..................... 134/10, 18, 30, 36, 134/37, 56 R, 95, 102, 25.1, 21, 25.2, 25.4, 1; 422/101, 102, 128, 295, 20, 26, 33

[56] References Cited

U.S. PATENT DOCUMENTS

| | | | |
|---|---|---|---|
| 4,193,818 | 3/1980 | Young et al. | 134/1 |
| 4,226,642 | 10/1980 | Baran | 134/10 |
| 4,576,792 | 3/1986 | Martensson | 134/36 |
| 4,670,061 | 2/1987 | Hanlegard | 134/18 |
| 4,710,233 | 12/1987 | Hohmann et al. | 134/18 |

Primary Examiner—Asok Pal
Attorney, Agent, or Firm—Kirkpatrick & Lockhart

[57] ABSTRACT

A method of operating a washer-sterilizer comprises the steps of: loading a chamber with items to be washed; filling the chamber to a predetermined level with a washing fluid; controllably injecting a steam or an air steam mixture into the chamber during the filling of the chamber with the washing fluid, the steam being injected in a turbulent manner to create a washing action and to begin heating the washing fluid; and continually injecting steam into the chamber after the chamber is filled to the predetermined level so as to subject the items to a washing action. After the washing phase, the chamber is drained, the items are rinsed, and the chamber is drained again. A unique piping arrangement is also disclosed.

14 Claims, 2 Drawing Sheets

WASHER-STERILIZER

BACKGROUND OF THE INVENTION

1. Field of the Invention

The present invention is directly generally to washers and more specifically to washer-sterilizers of the type used to wash and sterilizer material in a hospital or laboratory.

2. Description of the Prior Art

Apparatus for washing and sterilizing are known. For example, in U.S. Pat. No. 4,226,642 to Baran an apparatus and method are disclosed for decontamination washing and/or biocidal treatment of articles. Air is injected at the bottom of the chamber to provide interaction through horizontally oriented discharges. Such interaction includes the formation of turbulent vortices. Upward movement of the air creates vertically oriented cleaning turbulence. Spray means are provided to remove loose soil before washing and to remove soil separated by washing. The washing phase may be followed by a steam sterilization cycle.

Another known washer-sterilizer is the Eagle 2000 PIWS which is available commercially from the American Sterilizer Company of Erie, Pa. That device is capable of subjecting materials placed within its chamber to a wash cycle, a flash cycle, or a washer-sterilize cycle as is known.

Although commercially available devices function very well, efficiency conscious customers are continually seeking washer-sterilizers with shorter cycle times. Shorter cycle times result in materials being placed back into service sooner, which ultimately results in less money been spent on inventories. An example of shorter cycle times is the government's specifications which require that the wash-sterilize cycle of a PIWS unit must be less than twenty-six minutes when a 75° F. (24° C.) eight and one-half minute wash cycle and a 270° F. (132° C.) three minute sterilize cycle is run. Such shorter cycle times make it increasingly more difficult for commercially available washer-sterilizers to satisfactorily wash and sterilize materials. Thus the need exists to improve the performance of known washer-sterilizers.

SUMMARY OF THE PRESENT INVENTION

The present invention is directed to the washing feature of a washer-sterilizer and includes an apparatus for washing and a method of operating the apparatus such that reduced cycle times can be achieved while improving performance. The method of operating the apparatus comprises the steps of: loading a chamber with items to be washed; filling the chamber to a predetermined level with a washing fluid; controllably injecting steam into the chamber during the filling of the chamber with the washing fluid, the steam being injected in a turbulent manner to create a washing action and to begin heating the washing fluid; and continually injecting steam into the chamber after the chamber is filled to the predetermined level so as to subject the items to a washing action. After the washing phase, the chamber is drained, the items are rinsed, and the chamber is drained again.

By controllably injecting steam in a turbulent manner into the chamber before the chamber is filled with the washing fluid, the process of raising the temperature of the washing fluid to the temperature needed for washing is begun. Previously, the injection of steam into the chamber before the items were completely submerged was believed to be detrimental to the washing process because the steam could "bake" soil onto the items which were not completely submerged. It was discovered, however, that a partially filled chamber could accept steam through the washing ejectors. The washing fluid condenses the steam immediately and prevents baking of soil on those items not submerged. Additionally, the turbulent action begins to wash items already covered by the washing fluid.

The method also includes the step of intermittently injecting water and steam into the chamber while the chamber is being drained. Previously, the injection of steam into the chamber during the draining phase was believed to be detrimental to the washing cycle because the steam could bake soil onto exposed items. However, the water removes any soil left form the washing cycle and prevents soil from being baked onto the items while the steam helps to force the washing fluid down the drain in a manner faster than that achieved by relying solely upon gravity.

The present invention also includes an apparatus comprised of a chamber capable of receiving items to be washed. Spray nozzles are provided for filling the chamber to a predetermined level with a washing fluid. Steam ejectors are provided for injecting steam into the chamber in a turbulent manner. Sensors monitor the operating parameters of the apparatus. A controller, which may include a microprocessor, is responsive to the sensors for controlling the operation of the spray nozzles and the steam ejectors such that steam is controllably injected into the chamber after a certain point during the filling of the chamber with the washing fluid to create a washing action and to begin heating the washing fluid. Steam is continually injected into the chamber after the chamber is filled to the predetermined level so as to subject the items to a washing action. A drain valve and a drain line are responsive to the microprocessor for draining the chamber.

The drain line carries a temperature sensor which monitors the temperature of the washing fluid in the drain line. However, because of differences in volume and construction between the drain line and the chamber, the washing fluid in the drain line will loose heat faster than the washing fluid in the chamber. To minimize such temperature variations, an overflow line is provided which is in fluid communication with the drain line. The chamber is periodically controllably overfilled causing washing fluid to flow through the drain line and the overflow line thereby exposing the temperature sensor to additional washing fluid having a temperature substantially equal to that of the temperature of the washing fluid in the chamber.

In the prior art, the temperature sensor is subjected to a continuous flow due to a draining or siphoning of washing fluid from the chamber. That lowered the washing fluid level to the extent that some items were exposed thereby reducing the efficacy of the washing cycle. The reduced washing fluid level often resulted in excessive end of cycle wash temperatures which was also detrimental to the washing cycle. In the present invention, the maintained washing fluid level narrows the washing temperature deviation during a washing cycle thereby improving efficiency.

By placing the temperature sensor in the drain and providing an overflow line, the piping of the washer-sterilizer is simplified which results in lower manufacturing costs. The resultant machine is easier to manufacture and service. By operating the washer-sterilizer according to the method described above, shorter cycle times are achieved. Those and other advantages and benefits of the present invention will become apparent from the Description of a Preferred Embodiment hereinbelow.

BRIEF DESCRIPTION OF THE DRAWINGS

In order that the present invention may be clearly understood and readily practiced, a preferred embodiment will be described, by way of example only, in conjunction with the following figures wherein.

DESCRIPTION OF A PREFERRED EMBODIMENT

Figure 1:
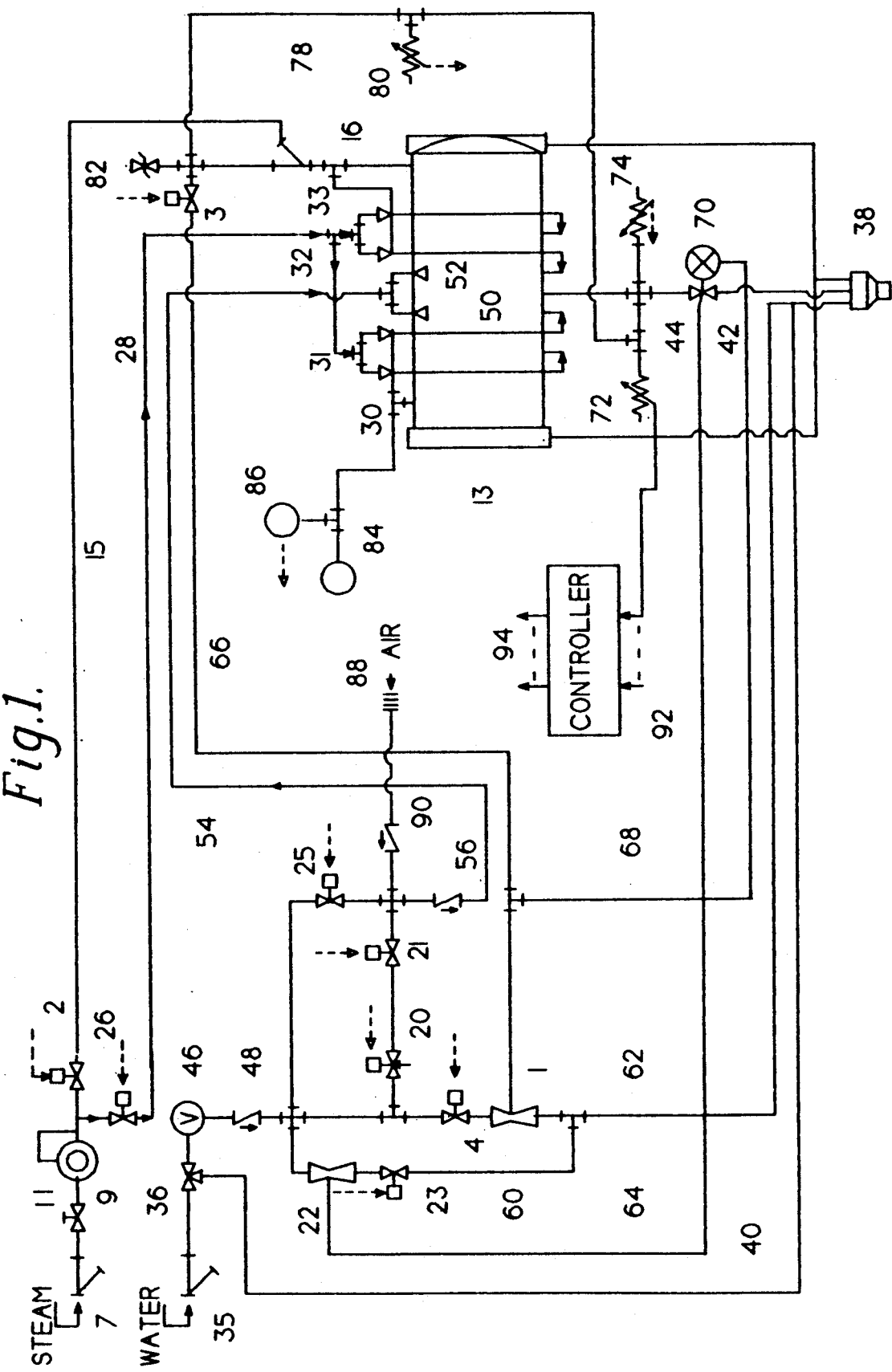
FIG. 1 is a piping diagram of the washer-sterilizer of the present invention.

In FIG. 1, a piping diagram of a washer-sterilizer 5 constructed according to the teachings of the present invention is illustrated. Although the present invention is described in conjunction with the washer-sterilizer 5, the principles of the present invention are equally applicable to dedicated washers.

Steam is supplied to a pressure regulator 11 through a strainer 7 and a steam supply valve 9. From the pressure regulator 11, the steam may be admitted to a chamber 13 through one of two paths. The first path includes a pair of steam to chamber lines 15 and 16 and a steam to chamber valve 2 which controls the flow of steam therethrough. The second path is through a steam to jet compressor line 28 which supplies steam to a pair of front ejectors 30 and 31 and a pair of rear ejectors 32 and 33 when a steam to jet compressor valve 26 is opened. The front and rear ejectors, 30 through 33, are known mechanical devices which inject a steam and air mixture through openings in the bottom of the chamber 13 in a turbulent manner. The bottom of the chamber 13 is connected to a waste drain 38 through a drain valve 42 and a drain line 44.

Water is input to the washer-sterilizer 5 through a strainer 35 and a water supply valve 36. The water supply valve 36 may be connected to the waste drain 38 through a line 40. The water supply valve 36 may also be connected to a vacuum breaker 46 and a one way check valve 48.

From the check valve 48, water is supplied to a pair of nozzles 50 and 52 located in the chamber 13 through a water supply line 54. The flow of water through the water supply line 54 is controlled by a chamber water valve 25. The water supply line 54 also has a one way check valve 56. A source of filtered air may be connected between the chamber water valve 25 and the check valve 56 through a filter 88 and a check valve 90. A line 58 is provided to allow the flow of water from the check valve 48 to bypass the chamber water valve 25. The line 58 includes a detergent injector 20 and a detergent supply valve 21.

From the check valve 48, water may also be provided to a water injector 22. Water is provided to the injector 22 when a chamber drain valve 23, connected between the injector 22 and the drain 38 through a pair of lines 60 and 62, is open. The ejector 22 controls the operation of the drain valve 42 through a line 64.

Finally, from the check valve 48, water may be provided to a water ejector 1 through an exhaust cooling valve 4. The ejector 1 is connected to the drain 38 through the line 62. The ejector 1 is in fluid communication with the top of the chamber 13 through a line 66 and the line 16 when a fast exhaust valve 3 is open.

The washer-sterilizer 5 is provided with an overflow line 68 connected between the ejector 1 and the drain valve 42 through a trap 70. The provision of the overflow line 68 is an important feature of the present invention and will be described in greater detail in conjunction with the description of the operation of the washer-sterilizer 5.

A low water level switch 72 and a temperature sensor such as a thermister 74 are in fluid communication with the drain line 44. Signals produced by the low water level switch 72 and the thermister 74 are input to a controller 76. The controller 76 may be a known type of microprocessor based controller.

A water level indicating line 78 is connected between the drain line 44 and the top of the chamber 13 through, for example, the line 16. The water level indicating line 78 carries a high water level switch 80 which produces a signal input to the controller 76. Because the water level indicating line 78 is in fluid communication with both the drain line 44 and the top of the chamber 13, the pressure above the water in the water level indicating line 87 is substantially the same as the pressure in the chamber 13 such that the water level in the water level indicating line 78 is substantially the same as the water level in the chamber 13. That enables the high water level switch 80 to provide an accurate indication of when a predetermined water level has been reached.

Completing the description of the piping diagram illustrated in FIG. 1, a safety valve 82 may be provided which is in fluid communication with the chamber 13. A pressure gauge 84 and a pressure transducer 86 may also be provided which are in fluid communication with the chamber 13. The pressure transducer 86 produces a signal representative of the pressure within the chamber 13 which is input to the controller 76.

In one embodiment of the invention, it is anticipated that the steam to chamber valve 2, fast exhaust valve 3, exhaust cooling valve 4, detergent supply valve 21, chamber drain valve 23, chamber water valve 25, and steam to jet compressor valve 26 may be a solenoid type of valve which can be remotely controlled by signals produced by the controller 76. Thus, it can be seen that the controller 76 receives input signals 92 from the low water level switch 72, thermister 74, high water level switch 80, and pressure transducer 86. From those input signals 92 and the controller's preprogrammed instructions, the controller produces output signals 94 capable of opening and closing the aforementioned solenoid operated valves in order to effect a desired wash or washer-sterilize cycle. Such controllers are well known in the art.

Figures 2, 2A:
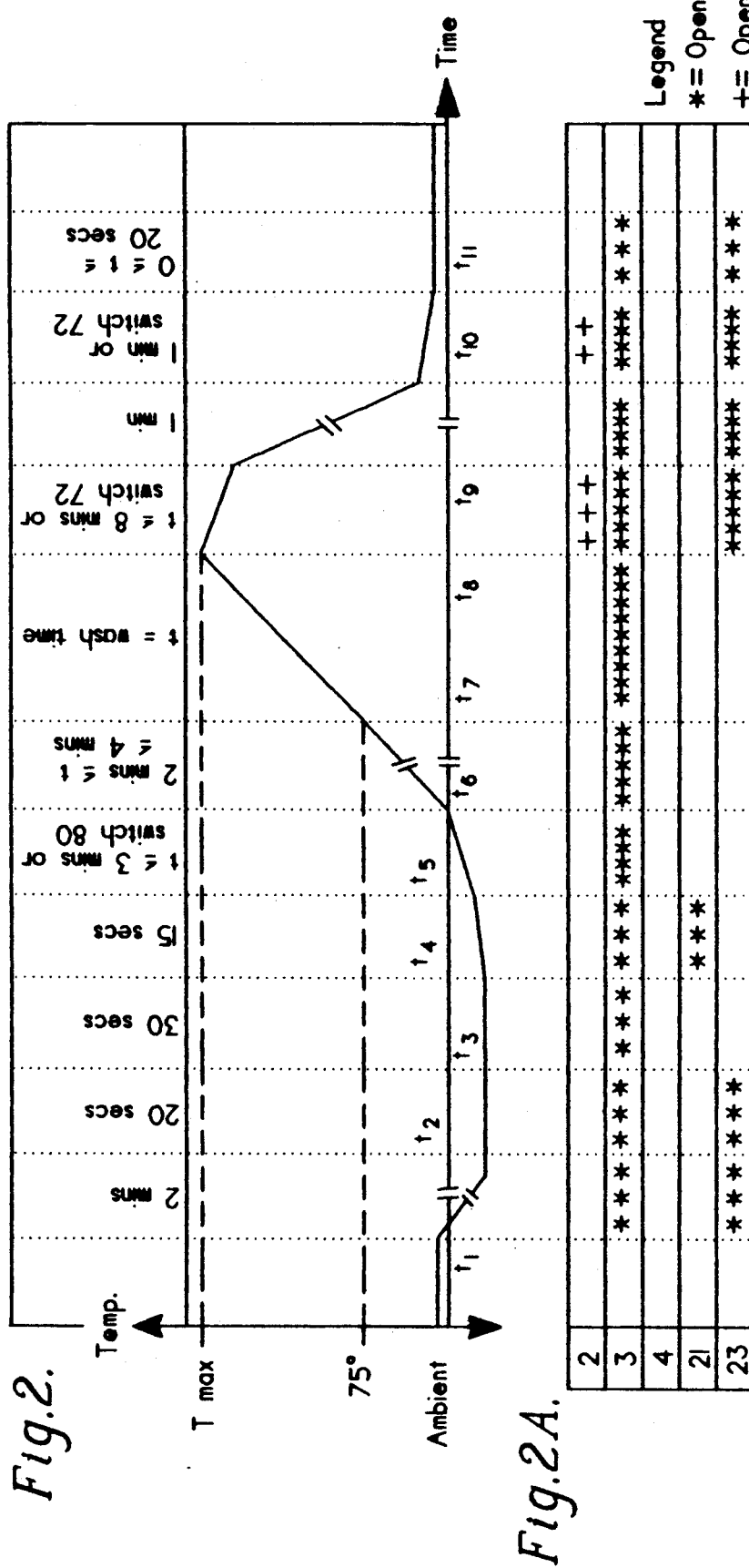
FIG. 2 is a graph illustrating the temperature as a function of time during a complete wash cycle.
FIG. 2A illustrates the status of various valves shown in FIG. 1 during the wash cycle shown in FIG. 2.

The operation of the washer-sterilizer 5 illustrated in FIG. 1 will now be described in conjunction with FIGS. 2 and 2a. FIG. 2 is a graph illustrating the temperature within the chamber 13 as a function of time during a wash cycle while FIG. 2a illustrates the status of various valves, i.e. open or closed, which are necessary to effect the wash cycle.

At the beginning of the wash cycle, the temperature within the chamber 13 is at ambient or room temperature while the items to be washed are loaded within the chamber. After the chamber has been loaded and the door closed, a rinse phase may begin at time $t_1$. To achieve the rinse, the fast exhaust valve 3, chamber drain valve 23, and chamber water valve 25 are open for approximately two minutes. After the first rinse is complete at time $t_2$, a first drain phase begins by closing the chamber water valve 25. The first drain phase may last for twenty seconds.

At time $t_3$, the chamber 13 begins filling with water by opening the chamber water valve 25. During that time, the chamber drain valve 23 is closed. That filling phase may last for approximately thirty seconds. After thirty seconds, the chamber water valve 25 is closed and the detergent supply valve 21 is open so that water carrying detergent is input to the chamber 13. According to this exemplary wash cycle, it takes fifteen seconds to supply the chamber 13 with sufficient detergent. Thereafter, at time $t_5$, the detergent supply valve 21 is closed and the chamber water valve 25 is reopened and the chamber is filled until either the high water level switch 80 indicates that the chamber is filled to the desired predetermined level or until three minutes elapse. Once the chamber 13 is full as indicated by the high water level switch 80, the chamber 13 is overfilled for an additional eight seconds so that water in the chamber overflows and goes down the drain line 44 where the thermistor 74 is located.

With the water level achieved by time $t_4$, it was determined experimentally that steam and air could be injected into the bottom of the chamber to begin heating the water, chamber, and items being washed. Such injection would also begin washing of the already submerged items by virtue of the agitation from the steam and air. Accordingly, during the detergent phase, from times $t_4$ to $t_5$, the temperature of the water is monitored and if it is found to be less than 68° F. (20° C.), then the steam to jet compressor valve 26 is controllably opened. That begins to heat the water to bring its temperature up to the temperature needed for washing, which is 75° F. (24° C.). Similarly, during the fill phase from times $t_5$ to $t_6$, the temperature of the water is monitored and if it is less than 70° F. (21° C.), then the steam to jet compressor valve 26 is controllably opened to increase the temperature of the water within the chamber 13. Also, during the periods from time $t_4$ to $t_5$ and time $t_5$ to $t_6$ certain of the items within the chamber will already be covered with water such that those items experience a washing action whenever the steam to jet compressor valve 26 is open.

At time $t_6$, the chamber 13 is filled to the desired predetermined level and a prewash phase is begun by opening the steam to jet compressor valve 26. That allows the steam to be continually injected into the chamber 13 in a turbulent manner so as to expose the items in the chamber to a washing action. The prewash phase lasts between two and four minutes and is ended when the temperature is greater than or equal to 75° F. (24° C.).

The wash phase then begins at time $t_7$ and continues until time $t_8$ which is the wash time selected by the user. During that time period, the steam to jet compressor valve 26 remains open so that a steam and air mixture is continually injected in a turbulent manner into the chamber 13. During both the prewash and wash phases, the chamber water valve 25 is periodically opened. For example, from time $t_6$ to time $t_7$, the valve 25 may be opened every thirty seconds and stay open for about three seconds. During the period from time $t_7$ until time $t_8$, the valve 25 may be opened every thirty seconds and stay open for approximately one second. The purpose of that periodic opening of the water chamber valve 25 is to overfill the chamber 13. When the chamber 13 is overfilled, water flows through the first chamber of the drain valve 42, through the trap 70, and the drain line 68. That flow of water replaces the cooler water surrounding the thermister 74 with water from the chamber 13 thereby causing the drain line 44 temperature to more closely follow the chamber 13 temperature. The continual addition of cooler water also helps to absorb the heat energy released by the condensing steam and prevents the wash from getting too hot. At time $t_8$ the wash phase is complete and a drain phase is initiated by opening chamber drain valve 23. The drain phase lasts until a signal is received from the low water level indicating switch 72 that the chamber is drained or for eight minutes, whichever occurs first. During the first sixty seconds of the drain phase, the steam to chamber valve 2 is controllably opened. Steam to chamber valve 2 remains open as long as the chamber pressure is below two psig and then closes at the end of the sixty seconds. That blows the water out of the drain line 44 and reduces the time required for draining the chamber 13. Additionally during the drain phase, the chamber water valve 25 is periodically opened so that water is sprayed onto the load, for example, at twelve second intervals for three seconds. Such a spray of water removes soil loosened during the wash phase. The steam to chamber valve 2 may also be intermittently opened to inject steam into the chamber 13 in conjunction with the opening of the chamber water valve 25 as shown in FIG. 2a.

Once the drain phase is complete at time $t_9$, a final rinse is performed which may last, for example, for one minute. That is accomplished by opening chamber water valve 25. After the one minute has elapsed, at time $t_{10}$, the chamber 13 is drained for one minute or until a signal is received from the low water level switch 72. During that drain phase, steam to chamber valve 2 may be controllably opened if the pressure in the chamber 13 falls below two psig. Whenever the steam to chamber valve 2 is open, the chamber water valve is also controllably opened to prevent the load from being overheated.

At time $t_{11}$, if this were a wash/sterilize cycle, then the controller 76 would begin the sterilization cycle. However, if only a wash cycle is being performed as illustrated in FIG. 2a, the fast exhaust valve 3 and the chamber drain valve 23 remain open for no more than twenty seconds. During that time, various parameters can be verified by the controller 76 such as the status of the valves, the duration of the overall wash cycle, etc. Thereafter, the items can be unloaded from the chamber 13.

In summary, the present invention is directed to a washer-sterilizer and a method of operating same. The washer-sterilizer has an improved piping design which results in a cost reduction and the resultant machine is easier to manufacture and service. The method of the present invention enables the washer-sterilizer to meet more stringent cycle times while increasing the cleaning capability of the washer-sterilizer.

While the present invention has been described in conjunction with a preferred embodiment thereof, modifications and variations will be apparent to those of ordinary skill in the art. This disclosure and the following claims are intended to cover all such modifications and variations.

What we claim is,

1. A method of operating a washing apparatus, comprising the steps of:
   loading a chamber with items to be washed;
   filling said chamber to a predetermined level covering the items with a washing fluid;
   controllably injecting steam into said chamber during the filling of said chamber with said washing fluid, said steam being injected in a turbulent manner to create a washing action and to begin heating said washing fluid;
   continually injecting steam into said chamber after said chamber is filled to said predetermined level so as to subject the items to a washing action;
   draining said chamber a first time;
   rinsing the items; and
   draining said chamber a second time.

2. The method of claim 1 additionally comprising the step of periodically introducing washing fluid into said chamber while steam is continually being injected into said chamber to cause some of said washing fluid to flow through a drain line and an overflow line.

3. The method of claim 2 additionally comprising the step of sensing the temperature of the washing fluid in said drain line.

4. The method of claim 1 additionally comprising the step of introducing steam into said chamber during said first draining of said chamber.

5. The method of claim 4 additionally comprising the step of intermittently spraying the washed items with water during said first draining of said chamber.

6. The method of claim 5 additionally comprising the steps of intermittently spraying the washed items with water and intermittently introducing steam into said chamber during said second draining of said chamber.

7. The method of claim 1 wherein said step of filling said chamber with a washing fluid includes the steps of introducing water into said chamber, introducing water carrying a detergent into said chamber, and filling said chamber to said predetermined level covering the items with water.

8. A washing apparatus, comprising:
   a chamber capable of receiving items to be washed;
   means for filling said chamber to a predetermined level covering the items with a washing fluid;
   means for injecting steam into said chamber in a turbulent manner;
   sensor means for monitoring the operating parameters of the washing apparatus;
   control means, responsive to said sensor means, for controlling the operation of said means for filling the chamber and said means for injecting steam into said chamber such that steam is controllably injected into said chamber during the filling of said chamber with said washing fluid to create a washing action and to begin heating said washing fluid, and steam is continually injected into said chamber after said chamber is filled to said predetermined level so as to subject the items to a washing action; and
   means responsive to said control means for draining said chamber.

9. The apparatus of claim 8 wherein said means for draining said chamber includes a drain line and a drain valve responsive to said control means.

10. The apparatus of claim 9 wherein said sensor means includes a temperature sensor and a low washing fluid level switch each positioned in fluid communication with said drain line.

11. The apparatus of claim 10 additionally comprising an overflow line in fluid communication with said drain line, said control means causing said chamber to be periodically overfilled such that washing fluid flows through said drain line and said overflow line thereby exposing said temperature sensor to additional washing fluid.

12. The apparatus of claim 10 additionally comprising a fluid level indicating line in fluid communication with said drain line and the top portion of said chamber, and wherein said sensor means includes a high washing fluid level switch.

13. The method of claim 1 additionally comprising the step of intermittently spraying the items to be washed with water from above during said step of controllably injecting steam into said chamber.

14. The apparatus of claim 8 additionally comprising means for spraying the items to be washed with water from above, and wherein said controls means is responsive to said sensor means for intermittently spraying the items to be washed with water from above while said steam is controllably injected into said chamber.

* * * * *

UNITED STATES PATENT AND TRADEMARK OFFICE
CERTIFICATE OF CORRECTION

PATENT NO. : 5,032,186

DATED : July 16, 1991

INVENTOR(S) : Robert W. Childers and Conrad J. Geibel

It is certified that error appears in the above-identified patent and that said Letters Patent is hereby corrected as shown below:

Col. 1, line 6, delete "directly" and substitute --directed-- therefor.

Col. 1, line 34, delete "been" and substitute --being-- therefor.

Col. 2, line 17, delete "form" and substitute --from-- therefor.

Col. 5, line 26, delete "thermistor" and substitute --thermister-- therefor.

Col. 8, line 43, delete "controls" and substitute --control-- therefor.

Signed and Sealed this

Fifth Day of January, 1993

Attest:

DOUGLAS B. COMER

*Attesting Officer*   *Acting Commissioner of Patents and Trademarks*